(12) United States Patent
Seifert et al.

(10) Patent No.: US 7,187,982 B2
(45) Date of Patent: Mar. 6, 2007

(54) MEDICAL ELECTRICAL LEAD ANCHORING

(75) Inventors: Kevin R. Seifert, Forest Lake, MN (US); Timothy G. Laske, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 5 days.

(21) Appl. No.: 10/637,160

(22) Filed: Aug. 8, 2003

(65) Prior Publication Data

US 2005/0033394 A1 Feb. 10, 2005

(51) Int. Cl.
*A61N 1/00* (2006.01)
(52) U.S. Cl. .................................................. 607/126
(58) Field of Classification Search ........ 607/116–128; 600/374–375, 377
See application file for complete search history.

(56) References Cited

U.S. PATENT DOCUMENTS

| | | | | |
|---|---|---|---|---|
| 3,244,174 A | 4/1966 | Wesbey et al. | ............. | 128/418 |
| 3,474,791 A | 10/1969 | Bentov | ......................... | 128/418 |
| 3,485,247 A | 12/1969 | Ackerman | .................. | 128/418 |
| 3,516,412 A | 6/1970 | Ackerman | .................. | 128/418 |
| 4,144,889 A | 3/1979 | Tyers et al. | .................. | 128/418 |
| 4,273,137 A * | 6/1981 | Pravoverov et al. | ........ | 607/116 |
| 4,341,226 A | 7/1982 | Peters | ......................... | 128/784 |
| 4,490,326 A | 12/1984 | Beroff et al. | .......... | 264/328.16 |
| 4,633,880 A | 1/1987 | Osypka et al. | .............. | 128/642 |
| 4,972,833 A | 11/1990 | Wildon | .................... | 128/419 P |
| 5,086,787 A * | 2/1992 | Grandjean et al. | .......... | 607/120 |
| 5,217,027 A * | 6/1993 | Hermens | .................... | 607/126 |
| 5,314,463 A | 5/1994 | Camps et al. | ............... | 607/129 |
| 5,350,419 A | 9/1994 | Bendel et al. | .............. | 607/132 |
| 5,489,294 A * | 2/1996 | McVenes et al. | ........... | 607/120 |
| 5,716,392 A | 2/1998 | Bourgeois et al. | .......... | 607/132 |
| 5,792,217 A | 8/1998 | Camps et al. | ............... | 607/119 |
| 5,871,528 A | 2/1999 | Camps et al. | ............... | 607/119 |
| 5,922,015 A | 7/1999 | Schaldach | .................... | 607/126 |
| 6,173,206 B1 | 1/2001 | Shchervinsky | .............. | 607/132 |
| 6,292,704 B1 * | 9/2001 | Malonek et al. | ............ | 607/121 |
| 6,360,130 B1 * | 3/2002 | Duysens et al. | ............ | 607/132 |
| 6,370,434 B1 | 4/2002 | Zhang et al. | ............... | 607/122 |
| 6,516,230 B2 | 2/2003 | Williams et al. | ........... | 607/116 |
| 2002/0072737 A1 | 6/2002 | Belden et al. | ................ | 606/34 |

* cited by examiner

*Primary Examiner*—Mark Bockelman
(74) *Attorney, Agent, or Firm*—Carol F. Barry; Girma Wolde-Michael (57) ABSTRACT

A non-rigid tether extends distally from an electrode of a medical electrical lead body coupling a tissue anchor to the lead body. The tissue anchor includes a surface to receive a push force from an insertion tool adapted to insert the anchor within a segment of tissue so that the electrode is held in close proximity to the tissue.

23 Claims, 7 Drawing Sheets

MEDICAL ELECTRICAL LEAD ANCHORING

TECHNICAL FIELD

The present invention generally relates to medical electrical leads and more particularly to means for anchoring distal portions of such leads.

BACKGROUND

Electrical stimulation of body tissue and organs is often used as a method of treating various conditions. Such stimulation is generally delivered by means of electrical contact between a pulse generator device and a target site via one or more medical electrical leads connected to the pulse generator device; leads typically include one or more stimulation electrodes joined to a distal portion of the lead, which are positioned and anchored in proximity to the target site. Various lead structures and methods for positioning and anchoring lead electrodes in proximity to target sites have been developed over the years. New structures and methods are necessary to anchor lead electrodes for emerging therapy delivery requirements, examples of which include cardiac resynchronization therapy wherein it may be desirable to implant an electrode in or on myocardial tissue via an epicardial approach. Embodiments of the present invention are described herein in the context of an epicardial implant, however those skilled in the art of implantable medical devices will recognize that embodiments of the present invention may be implemented in a host of other therapy delivery contexts.

BRIEF DESCRIPTION OF THE DRAWINGS

The following drawings are illustrative of particular embodiments of the invention and therefore do not limit the scope of the invention, but are presented to assist in providing a proper understanding. The drawings are not to scale (unless so stated) and are intended for use in conjunction with the explanations in the following detailed description. The present invention will hereinafter be described in conjunction with the appended drawings, wherein like numerals denote like elements, and.

DETAILED DESCRIPTION OF THE DRAWINGS

The following detailed description is merely exemplary in nature and is not intended to limit the scope, applicability, or configuration of the invention in any way. Rather, the following description provides a convenient illustration for implementing exemplary embodiments of the invention.

Figure 1A:
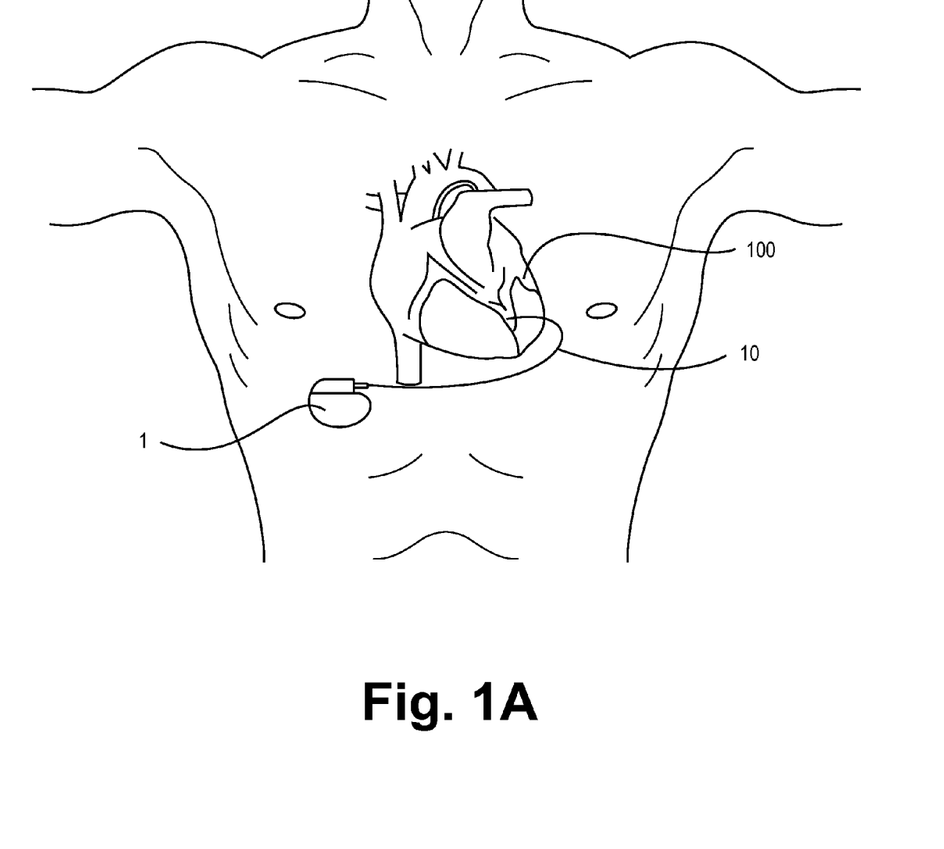
FIG. 1A is a schematic overview of an implantable medical device (IMD) including a medical electrical lead according to embodiments of the present invention.
Figure 1B:
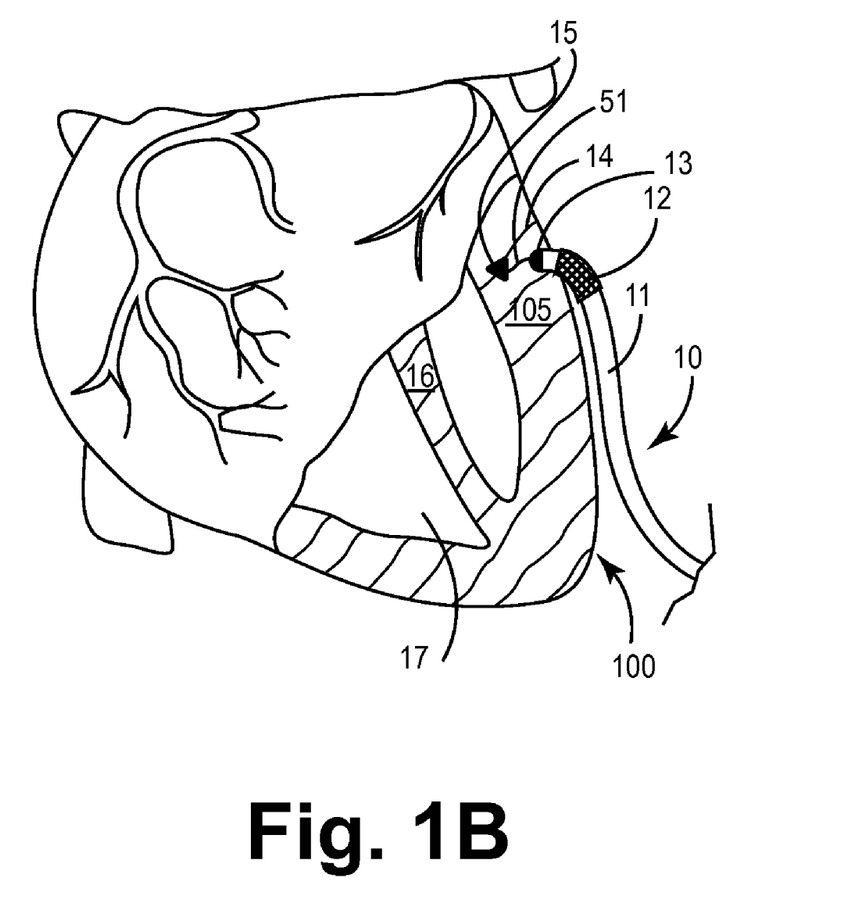
FIG. 1B is an enlarged detail from the schematic overview shown in FIG. 1A.

FIG. 1A is a schematic overview of an implantable medical device (IMD) including a medical electrical lead according to embodiments of the present invention. FIG. 1A illustrates an IMD including an implantable pulse generator (IPG) 1 coupled to a medical electrical lead 10, which in turn is coupled to a heart left side 100 for stimulation thereof. FIG. 1B is an enlarged detail showing salient portions of a distal portion of lead 10. FIG. 1B illustrates lead 10 including an electrode 13 coupled to a lead body 11 and implanted in a wall 105 of left heart 100; electrode 13 is coupled to IPG 1 via a conductor (not shown) extending within lead body to a connector contact (not shown) formed at a proximal end of lead 10, which is connected to IPG 1. According to embodiments of the present invention, as illustrated in FIG. 1B, lead 10 further includes a tissue anchor 15 coupled to lead 10 via a non-rigid tether 14 extending distally from electrode 13; tissue anchor 15 has been pushed into heart wall 105 followed by electrode 13. It should be noted that lead 10 might also be similarly implanted in a septal wall 16 approached from a right ventricle 17 via a transvenous route well known to those skilled in the art, or in any other wall of the heart.

Tissue anchor 15 includes a surface 51 to receive a push force, which will be further described herein below, according to embodiments of the present invention. According to some embodiments, anchor 15 is formed of a bioabsorbable material, examples of which include those taught in lines 10–24 of U.S. Pat. No. 6,173,206. One example of an appropriate bioabsorbable material, polydioxanone is described along with means for molding the material in U.S. Pat. No. 4,490,326, the relevant teachings of which are incorporated by reference herein.

FIG. 1B further illustrates means for promoting chronic adhesion to a surface of heart wall 105 embodied by a layer 12 formed about lead body 11. According to some embodiments of the present invention, layer 12 creates a porous or roughened surface on lead body 11, which encourages tissue ingrowth; examples of such a layer include a polyester mesh sleeve formed about lead body 11.

Figure 2A:
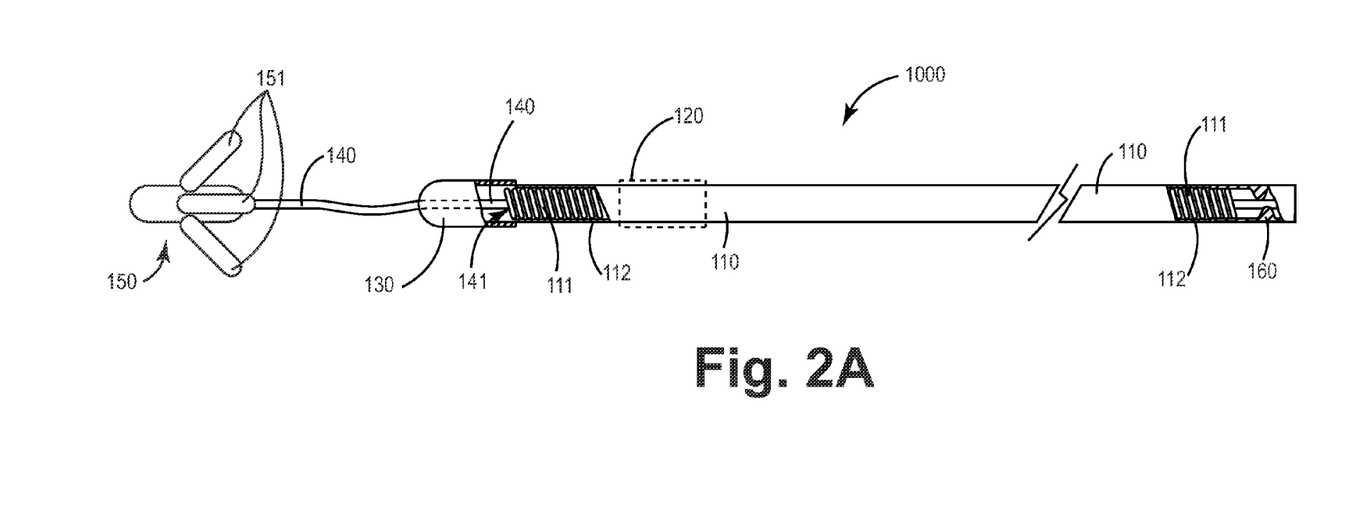
FIG. 2A is a plan view with partial section views of a medical electrical lead according to one embodiment of the present invention.

FIG. 2A is a plan view with partial section views of a medical electrical lead 1000 according to one embodiment of the present invention. FIG. 2A illustrates a lead body 110 including an optional layer 120 (indicated with dashed lines) as means previously described for promoting chronic adhesion, a conductor 111 and an outer insulative sheath 112; conductor 111 couples an electrode 130 to a connector contact 160 for coupling to an IPG, e.g. IPG 1 shown in FIG. 1A. Sheath 112 may be formed of a biocompatible polymer, examples of which include polyurethane and silicone rubber. Materials from which electrode 130 may be formed are well known to those skilled in the art and include platinum, gold, and tantalum; materials from which contact 160 may be formed are likewise known and include stainless steel and titanium; materials from which conductor 111 may be formed are likewise known and include MP35N alloy. Means for coupling conductor 111 to both electrode 130 and connector contact 160 include crimping and welding along with other methods known to those skilled in the art of lead construction.

FIG. 2A further illustrates a tissue anchor 150, including resilient tine members 151, joined to lead body 110 via a non-rigid tether 140 extending distally from electrode 130 according to one embodiment of the present invention. Tine members 151 may be formed from a polymer, for example polyurethane or silicone. Tether 140 and other tether elements described below in conjunction with alternate embodiments are formed from flexible materials, examples of which include, without limitation, nylon thread, polyethylene fiber, liquid crystal polymer fiber, polyester fiber, polypropylene wire, silicone rod or tube and polyurethane rode or tube. In the embodiment illustrated by FIG. 2A, tether 140 also extends through and proximally from electrode 130 through a lumen 141 formed within lead body 110 and is coupled to connector contact 160; thus lead body 110 generally conforms to lead body embodiments taught by Williams and Chivers in U.S. Pat. No. 6,516,230 wherein means for mechanically coupling a fiber cord to lead components are described. Construction methods taught by Williams and Chivers in the '230 patent, incorporated by reference herein, may be used to build embodiments of the present invention, both those wherein a fiber cord extending within lead body is used for a tether and those in which a tether extends only between an electrode and an anchor. In alternate embodiments a conductor is formed as a cable rather than a coil as illustrated in FIG. 2A. Furthermore, another embodiment according to the present invention includes an insulated portion of a cable conductor, which conductor couples electrode 130 to contact 160, extending distally of electrode to form tether 140 joining anchor 150 to lead body 110.

Figure 2B:
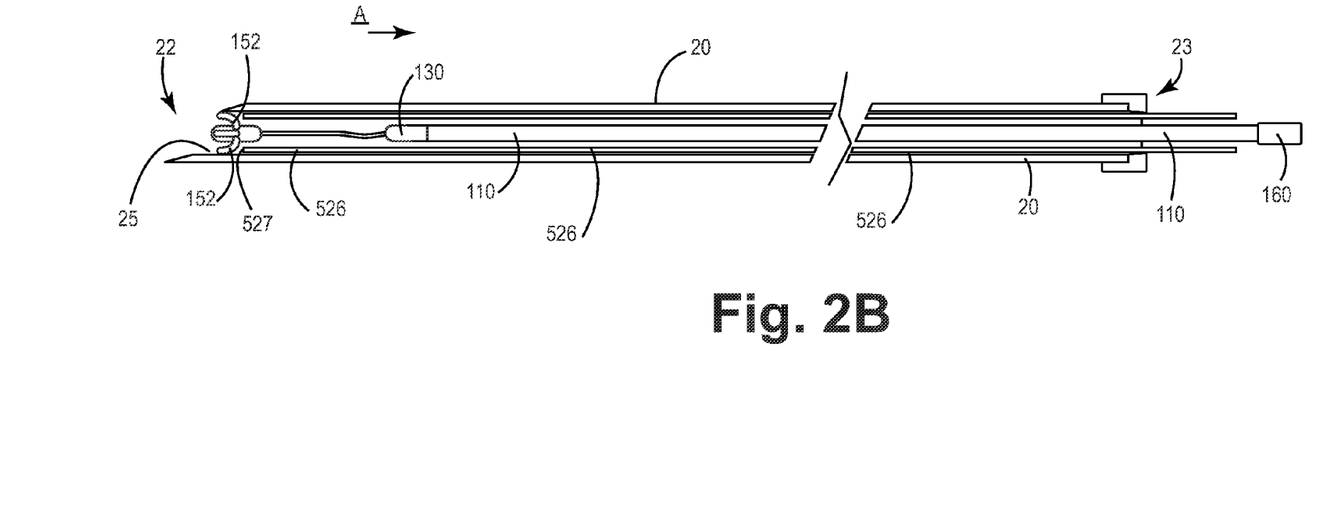
FIG. 2B is a partial section view of the lead shown in FIG. 2A assembled into an insertion tool according to one embodiment of the present invention.

FIG. 2B is a partial section view of lead 1000 assembled into an insertion tool according to one embodiment of the present invention. FIG. 2B illustrates the insertion tool as a needle 20 including a lumen 25 slidably engaging lead 1000, wherein tine members 151 have been folded distally when lead body 110 was pulled, in the direction of arrow A, into needle 20, having been inserted, connector contact 160 first, at a distal end 22 of needle 20. Alternately lead 1000 may be inserted into needle 20 at a proximal end 23 so that tines 151 are folded down in an opposite direction. According to this embodiment of the present invention, undersides 152 of tines 151 are laterally extending surfaces which comprise means for receiving a push force from a distal end 527 of a push tube 526 slideably engaged within lumen 25 of needle 20 and slideably engaged about lead 1000, in order to insert anchor 150 into a segment of tissue at a target site. Needle 20 and push tube 526 are preferably formed from a semi-rigid material, examples of which include, without limitation, a PEEK polymer and a super-elastic metal such as Nitinol.

Figure 3A:
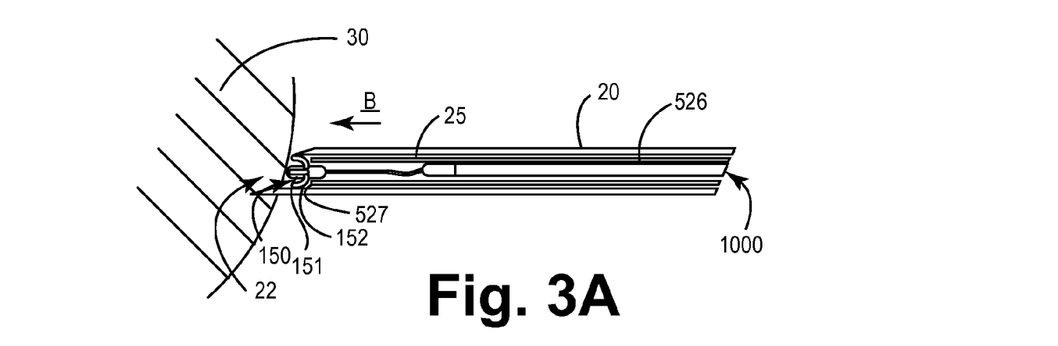
FIGS. 3A–C are schematics depicting implantation of a distal portion of the lead shown in FIG. 2A.
Figure 3B:
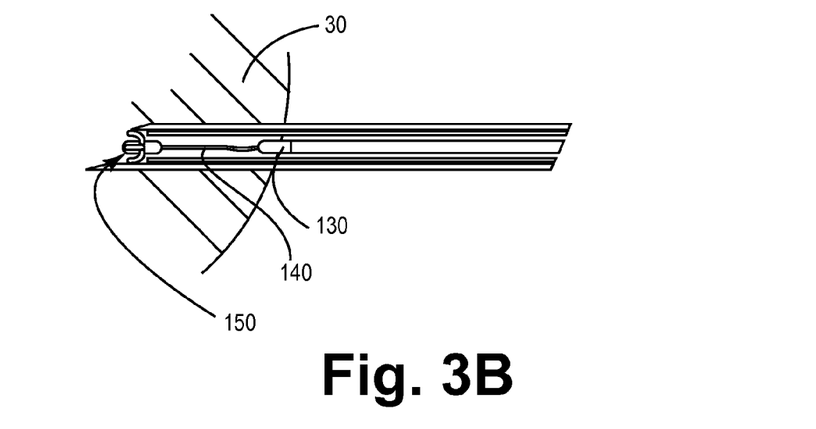
Figure 3C:
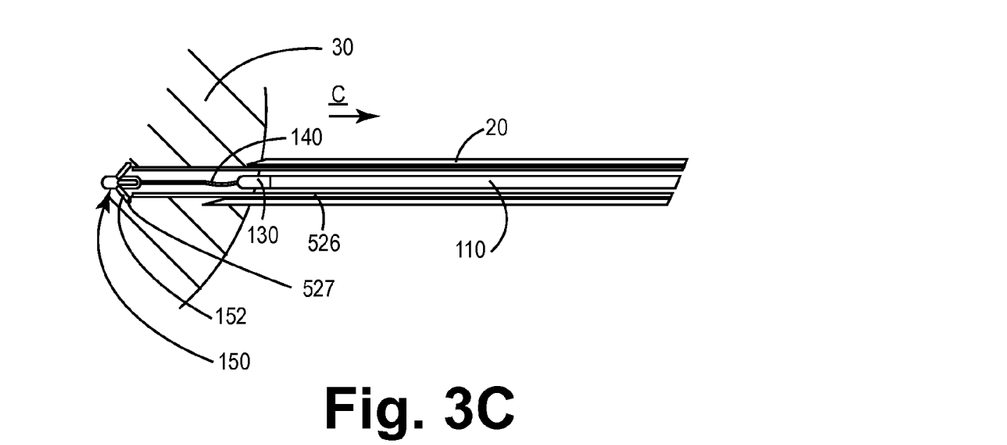

FIGS. 3A–C are schematics depicting insertion of anchor 150 into a segment of tissue 30. For convenience, needle 20 is shown herein having a substantially straight longitudinal axis, however it should be noted that the longitudinal axis of needle 20 may have any curvature facilitating piercing a wall of an organ without risk of perforating that wall, i.e. entry and exit at a same surface of the organ; some such curvatures are taught, in the context of epicardial leads, by Bourgeois et al. in commonly assigned U.S. Pat. No. 5,716, 392. Furthermore, means for gaining access to a target site for insertion of a lead via needle 20 are not illustrated but are well known to those skilled in the art of surgery, either conventional or minimally invasive.

FIG. 3A illustrates lead 1000 carried in lumen 25 of needle 20 as distal end 22 of needle 20 begins to pierce tissue 30. FIG. 3B illustrates needle 20 having carried anchor 150, tether 140 and electrode 130 into tissue 30 and FIG. 3C illustrates a removal of needle 20 over electrode 130 and lead body 110 leaving anchor 150, tether 140 and electrode 130 implanted in tissue 30. As previously described, underside 152 of tine 151 receives a push force from distal end 527 of a push tube 526 slideably engaged within lumen 25 of needle 20; the force, according to arrow B, carries lead 1000 forward in order to implant anchor 150, tether 140 and electrode in tissue 30. It should be noted that a depth of insertion may be varied from that illustrated such that electrode 130 is positioned at a surface 300 of tissue segment 30 rather than within tissue segment 30. Furthermore, although electrode 130 is described as terminating lead body 110 in the illustrated embodiment, electrode 130 need not terminate lead body 110; according to alternate embodiments an electrode is positioned more proximally along lead body and insertion depth corresponds to the position of the electrode in order to implant electrode in contact with tissue segment 30.

Figure 4:
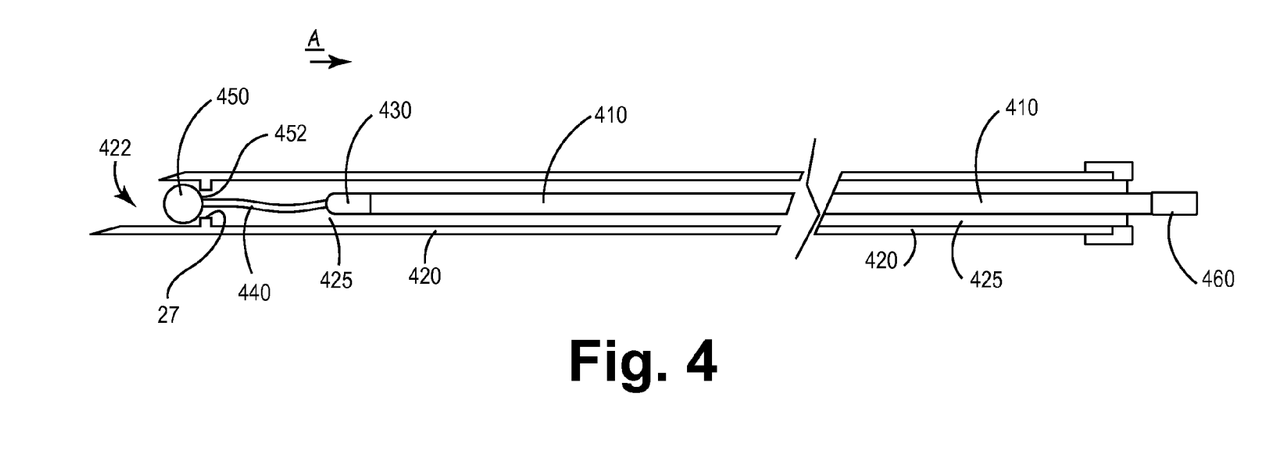
FIG. 4 is a partial section view of a lead and an insertion tool according to alternate embodiments.

FIG. 4 is a plan view with a partial section of a lead and an insertion tool according to additional alternate embodiments. FIG. 4 illustrates a lead body 410 terminated at a distal end with electrode 430 which is coupled to a connector contact 460 via a conductor within lead body 410 (not shown) and from which extends a non-rigid tether 440 joined to a tissue anchor 450 formed by a substantially spherical member. As with previous embodiments, a laterally extending surface 452 of anchor 450 is means for receiving a push force, however according to the alternate embodiment of an insertion tool, the push force is provided by a protrusion 27 extending into a lumen 425 of a needle 420 which is slideably engaged about lead body 410. In one embodiment, wherein tether 440 is formed from a nylon thread, melting a distal end of tether 440 integrally forms tissue anchor 450. According to the embodiment illustrated in FIG. 4, lead body 410 may be pulled, in the direction of arrow A, into needle 420, having been inserted, connector contact 460 first, at a distal end 422 of needle 420. Of course needle 20 and push tube 526 previously described may also be used as an insertion tool for the lead illustrated in FIG. 4.

Figure 5:
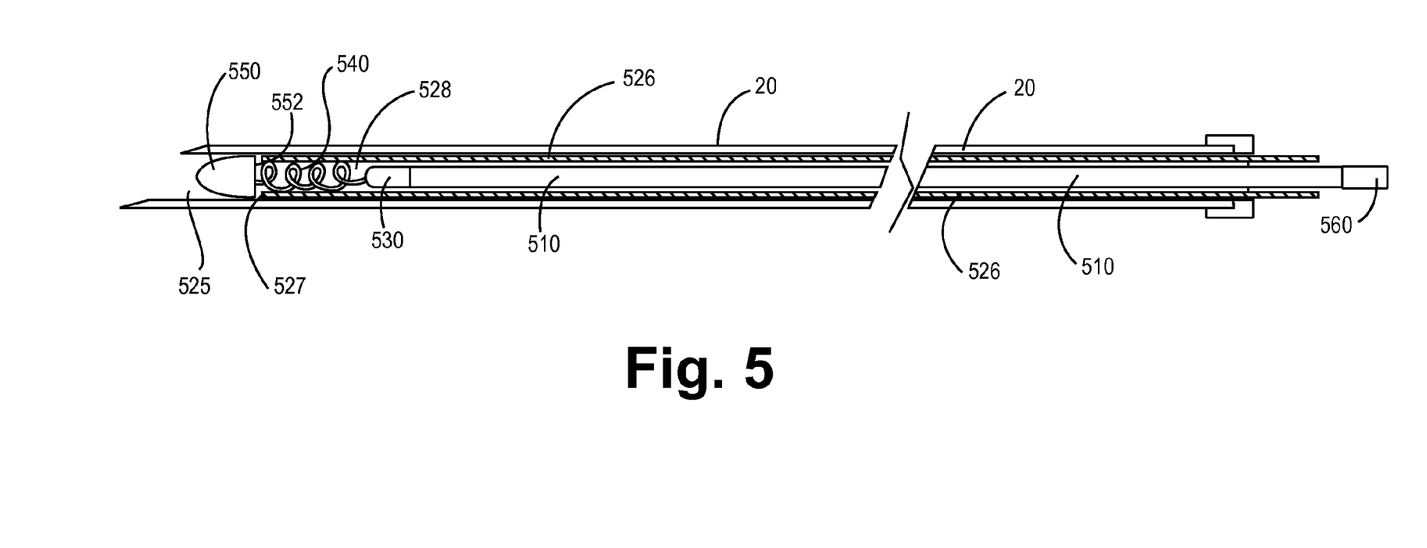
FIG. 5 is a partial section of a lead, according to an additional alternate embodiment, and the insertion tool of FIG. 2B.

FIG. 5 is a partial section of a lead, according to an additional alternate embodiment, assembled within the insertion tool of FIG. 2B. FIG. 5 illustrates a lead body 510 terminated at a distal end with electrode 530 which is coupled to a connector contact 560 via a conductor within lead body 510 (not shown) and from which extends a helically formed non-rigid tether 540 joined to a tissue anchor 550 formed by a substantially conical member. As with previous embodiments, laterally extending surface 552 of anchor 550 is means for receiving a push force provided by distal end 527 of push tube 526 slidably engaged about lead body 510 and slidably engaged within needle 20.

Figure 6:
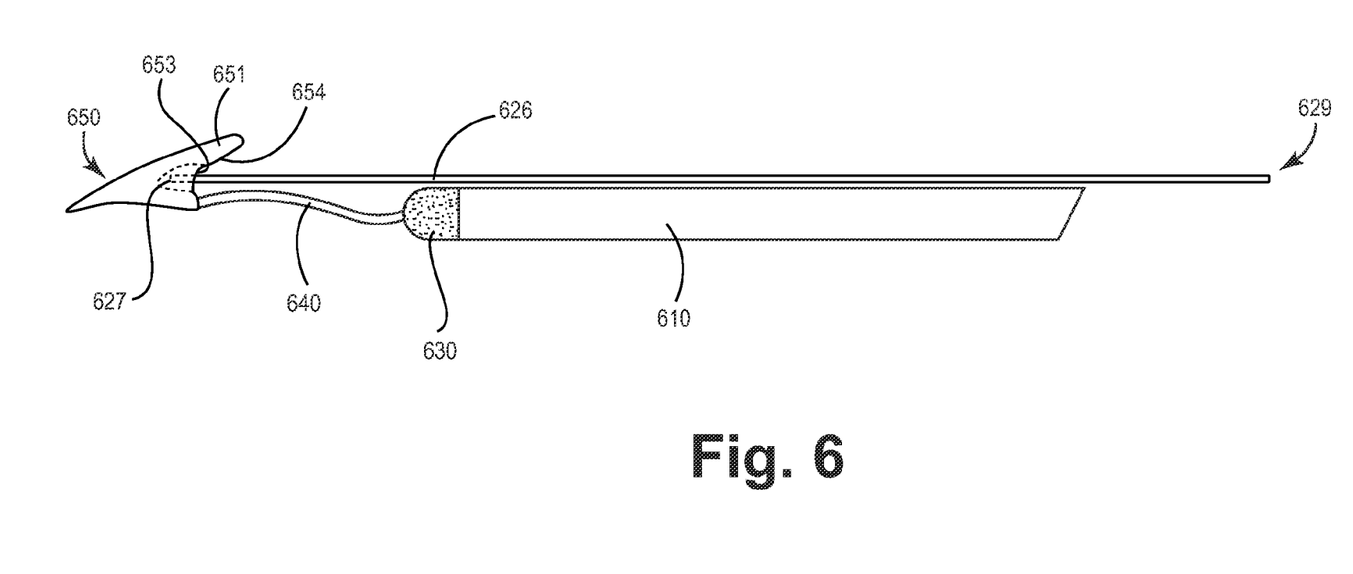
FIG. 6 is a plan view of a distal portion of a lead and an insertion tool according to another embodiment of the present invention.

FIG. 6 is a plan view of a distal portion of a lead and an insertion tool according to another embodiment of the present invention. FIG. 6 illustrates a lead body 610 terminated by an electrode 630 from which extends a tether 640 joined to a tissue anchor 650 including a resilient tine member 651 and a recess 653. According to embodiments of the present invention, FIG. 6 further illustrates recess 653 as means for receiving a push force from a distal end 627 of a stylet insertion tool 626 in order to insert tissue anchor 650 into a segment of tissue thus implanting electrode 630. Alternately, a needle insertion tool, e.g. needle 420, or a push tube within a needle, e.g. push tube 526 within needle 20, may be used to insert anchor 650 by engaging a laterally extending surface 654 of anchor 650 as previously described for other embodiments.

Figure 7:
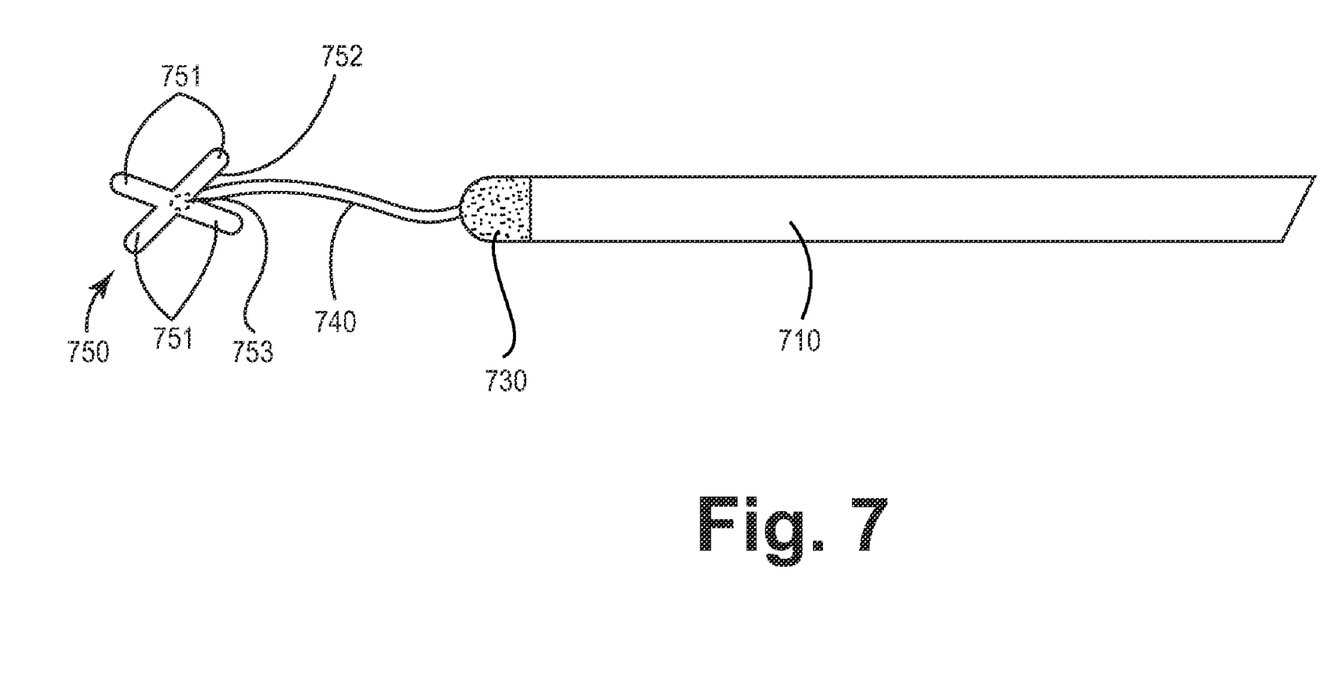
FIG. 7 is a plan view of a lead according to yet another embodiment of the present invention.

FIG. 7 is a plan view of a lead according to yet another embodiment of the present invention. FIG. 7 illustrates a lead body 710 terminated by an electrode 730 from which extends a tether 740 joined to a tissue anchor 750 including resilient tine members 751 and a recess 753. According to embodiments of the present invention, in order to implant electrode 730 by inserting tissue anchor 750 into a tissue segment, recess 753 comprises means for receiving a push force from a stylet insertion tool, e.g. stylet 626 and, according to alternate embodiments, laterally extending surface 752 comprises means for receiving a push force from a needle, e.g. needle 420, or a push tube, e.g. push tube 526.

In the foregoing specification, the invention has been described with reference to specific embodiments. However, it may be appreciated that various modifications and changes can be made without departing from the scope of the invention as set forth in the appended claims. Accordingly, the specification and figures are to be regarded as illustrative rather than as restrictive, and all such modifications are intended to be included within the scope of the present invention.

What is claimed is:

1. A medical electrical lead, comprising:
   a lead body including an elongated insulated conductor and an electrode coupled to the conductor;
   a non-rigid tether extending distally from the electrode and including a first end and a second end; the first end of the tether coupled to the lead body; and a tissue anchor terminating a distal end of the lead and coupled to the second end of the tether; the anchor including a surface which forms a recess for receiving a push force from an insertion tool adapted to insert the anchor within a segment of tissue so that the electrode is positioned in close proximity to the tissue.

2. The medical electrical lead of claim 1, wherein the lead body further includes a lumen extending therethrough and the tether further extends proximally from the electrode through the lumen.

3. The medical electrical lead of claim 2, wherein the tether comprises a polyester fiber cord.

4. The medical electrical lead of claim 1, wherein the tether comprises a material selected from the group consisting of nylon, polyester, polypropylene, polyethylene, liquid crystal polymer, silicone and polyurethane.

5. The medical electrical lead of claim 1, wherein the tether comprises a portion of the elongated insulated conductor.

6. The medical electrical lead of claim 1, wherein the tether forms a helix in between the electrode and the second end of the tether.

7. The medical electrical lead of claim 1, wherein the surface of the anchor extends laterally from the tether.

8. The medical electrical lead of claim 1, wherein the anchor comprises a resilient tine member.

9. The medical electrical lead of claim 1, wherein the anchor comprises a bioabsorbable material.

10. A medical implant system, comprising:
    a medical electrical lead body including an elongated insulated conductor and an electrode coupled to the conductor;
    a non-rigid tether extending distally from the electrode and including a first end coupled to the lead body and a second end;
    a tissue anchor coupled to the second end of the tether; and
    an insertion tool adapted to push the anchor into a segment of tissue in order to implant the electrode in proximity to the tissue;
    wherein the anchor includes a surface receiving the push from the insertion tool.

11. The implant system of claim 10, wherein, wherein the insertion tool comprises a needle including a lumen adapted to slideably engage the lead and the insertion tool further comprises a push tube slidably engaged within the needle lumen and slidably engaged about the lead; the push tube including a distal end interfacing with the surface of the anchor to push the anchor.

12. The implant system of claim 10, wherein the lead body further includes a lumen extending therethrough and the tether further extends proximally from the electrode through the lumen.

13. The implant system of claim 12, wherein the tether comprises a polyester fiber cord.

14. The implant system of claim 10, wherein the tether comprises a portion of the elongated insulated conductor.

15. The implant system of claim 10, wherein the tether is formed of a material selected from the group consisting of nylon, polyester, polypropylene, polyethylene, liquid crystal polymer, silicone and polyurethane.

16. The implant system of claim 10, wherein the tether forms a helix in between the electrode and the second end of the tether.

17. The implant system of claim 10, wherein the anchor comprises a bioabsorbable material.

18. The implant system of claim 10, wherein the anchor comprises a member selected from the group consisting of a resilient tine, a substantially spherical member, and a substantially conical member.

19. A medical implant system comprising:
    a medical electrical lead body including an elongated insulated conductor and an electrode coupled to the conductor;
    a non-rigid tether extending distally from the electrode and including a first end coupled to the lead body and a second end;
    a tissue anchor coupled to the second end of the tether, the anchor includes a surface receiving the push from the insertion tool; and
    an insertion tool adapted to push the anchor into a segment of tissue in order to implant the electrode in proximity to the tissue,
    wherein the insertion tool comprises a needle including a lumen adapted to slideably engage the lead, the needle further includes a protrusion extending into the lumen and interfacing with the surface of the anchor to push the anchor.

20. The medical electrical lead of claim 19, wherein the anchor comprises a substantially spherical member.

21. A medical implant system comprising:
    a medical electrical lead body including an elongated insulated conductor and an electrode coupled to the conductor;
    a non-rigid tether extending distally from the electrode and including a first end coupled to the lead body and a second end;
    a tissue anchor coupled to the second end of the tether, the anchor includes a surface receiving the push from the insertion tool; and
    an insertion tool adapted to push the anchor into a segment of tissue in order to implant the electrode in proximity to the tissue, the insertion tool comprises a needle including a lumen adapted to slideably engage the lead;

wherein the insertion tool further comprises a push tube slidably engaged within the needle lumen and slidably engaged about the lead; the push tube including a distal end interfacing with the surface of the anchor to push the anchor.

22. The medical electrical lead of claim 21, wherein the anchor comprises a substantially conical member.

23. A medical implant system comprising:
a medical electrical lead body including an elongated insulated conductor and an electrode coupled to the conductor;
a non-rigid tether extending distally from the electrode and including a first end coupled to the lead body and a second end;
a tissue anchor coupled to the second end of the tether, the anchor includes a surface receiving the push from the insertion tool; and
an insertion tool adapted to push the anchor into a segment of tissue in order to implant the electrode in proximity to the tissue, the insertion tool the insertion tool comprises a stylet including a distal end; and
the surface of the anchor forms a recess receiving the distal end of the stylet.

\* \* \* \* \*